（12）United States Patent
Nallathambi et al.

(10) Patent No.: US 11,534,108 B2
(45) Date of Patent: Dec. 27, 2022

(54) SCREENING DEVICE, METHOD, AND SYSTEM FOR STRUCTURAL HEART DISEASE

(71) Applicant: Vital Connect, Inc., San Jose, CA (US)

(72) Inventors: Gabriel Nallathambi, San Jose, CA (US); Ben Alexander, San Jose, CA (US); Nandakumar Selvaraj, San Jose, CA (US)

(73) Assignee: VITAL CONNECT, INC., San Jose, CA (US)

( * ) Notice: Subject to any disclaimer, the term of this patent is extended or adjusted under 35 U.S.C. 154(b) by 406 days.

(21) Appl. No.: 16/564,796

(22) Filed: Sep. 9, 2019

(65) Prior Publication Data

US 2020/0077951 A1 Mar. 12, 2020

Related U.S. Application Data

(60) Provisional application No. 62/728,199, filed on Sep. 7, 2018.

(51) Int. Cl.
| | |
|---|---|
| *A61B 5/00* | (2006.01) |
| *A61B 7/04* | (2006.01) |
| *A61B 5/25* | (2021.01) |

(52) U.S. Cl.
CPC .......... *A61B 5/6801* (2013.01); *A61B 5/0006* (2013.01); *A61B 5/25* (2021.01); *A61B 5/6823* (2013.01); *A61B 7/04* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 8,718,765 B2 * | 5/2014 | Baumann | A61B 5/7282 607/17 |
| 2003/0060723 A1 | 3/2003 | Joo et al. | |
| 2008/0234594 A1 * | 9/2008 | Brooks | A61B 5/683 600/513 |
| 2012/0245853 A1 * | 9/2012 | Baumann | A61B 5/02028 702/19 |
| 2013/0041268 A1 | 2/2013 | Rimoldi et al. | |
| 2014/0378849 A1 | 12/2014 | Krimsky et al. | |
| 2015/0164340 A1 * | 6/2015 | Bedingham | A61B 5/7405 600/484 |

(Continued)

FOREIGN PATENT DOCUMENTS

| | | |
|---|---|---|
| DE | 10 2008 037 919 A1 | 2/2010 |
| WO | 2017100188 A1 | 6/2017 |
| WO | 2017/214198 A1 | 12/2017 |

OTHER PUBLICATIONS

International Search Report and Written Opinion from International Application No. PCT/US2019/050207 dated Dec. 27, 2019.

(Continued)

*Primary Examiner* — Shirley X Jian
(74) *Attorney, Agent, or Firm* — Brundidge & Stanger, P.C.

(57) ABSTRACT

A wireless wearable sensor device, system, method, and non-transitory computer readable medium for screening for structural heart disease based on electrocardiogram, phonocardiogram, and/or accelerometer signals on a patient's skin surface.

16 Claims, 6 Drawing Sheets

(56) References Cited

U.S. PATENT DOCUMENTS

2017/0188869 A1 7/2017 Kale et al.
2018/0325407 A1* 11/2018 Varadan ................ A61B 5/339

OTHER PUBLICATIONS

Ricke, AD et al., "Automatic Segmentation of Heart Sound Signals Using Hidden Markov Models", Computers in Cardiology, 2005 Lyon, France Sep. 25-28, 2005, Piscataway, IEEE, NJ, USA, vol. 32, Sep. 25, 2005, pp. 953-956.
Alexander, Ben et al., "Screening of Heart Sounds Using Hidden Markov and Gammatone Filterbank Models", 2018 17th IEEE International Conference on Machine Learning and Applications (ICMLA), IEEE, Dec. 17, 2018, pp. 1460-1465.
European Supplementary European Search Report from EP Application No. 19856758.8 dated Mar. 22, 2022, 9 pages.

* cited by examiner

200

210 — Measure electrocardiogram, phonocardiogram, and accelerometer signals at patient's chest skin surface using wearable sensor device 220 — Divide signals into one or more sequences based on a measure of body acceleration 230 — Screening decisions on one or more sequences of electrocardiogram, and phonocardiogram derived features 240 — Determine sequence of aggregate screening decisions 250 — Combine individual decisions to screen for structural heart disease

Figure 2

SCREENING DEVICE, METHOD, AND SYSTEM FOR STRUCTURAL HEART DISEASE

CROSS-REFERENCE TO RELATED APPLICATIONS

This application claims the benefit of U.S. Provisional Patent Application No. 62/728,199, filed on Sep. 7, 2018, entitled "SCREENING FOR STRUCTURAL HEART DISEASE," which is incorporated herein by reference in its entirety.

FIELD OF THE INVENTION

The present invention relates to medical devices, and more particularly, to screening of structural heart disease using a wearable sensor device measuring one or more leads of electrocardiogram, phonocardiogram, and accelerometer signals at chest skin surface.

BACKGROUND

Auscultation is a technique for listening to sounds associated with functioning of internal organs such as the heart, lungs and intestines using a stethoscope; and it is one of a physician's fundamental diagnostic tools. The sounds, produced predominantly by the closure of atrio-venticular and semilunar heart valves, and the manual heart auscultation, provide a glimpse of cardiac diagnosis on the structural and functional health of the heart. However, the traditional stethoscope used as a spot check diagnostic tool relies on the physician's skill and experience, and therefore is inherently limited by the human threshold of audibility in perceiving sounds of only certain magnitude and bandwidth; further, capturing sound data records for future reference are not possible.

Advances in objective heart sound analysis using electronic recordings are crucial as more than 5 million people in the U.S. are diagnosed with heart valve disease every year. With an aging population, acquired structural heart diseases such as calcific aortic valve stenosis and mitral regurgitation are the third most common cardiovascular disease. Adult patients with aortic stenosis are about 1.5 million in U.S. and 56% of them are over 70 years old in Europe. Besides, congenital heart disease, the most common condition with structural heart defects at birth, affects more than 71,000 children in the U.S. and European Union every year. Effective medical management and surgical treatment planning for structural or congenital heart disease may necessitate objective and reliable monitoring of functions of the heart including heart sounds.

With the advent of digital stethoscopes, clinicians are now able to record heart sounds as digital waveforms, and include a visual component, beyond listening, to the examination. Heart sound recordings, known as phonocardiograms (PCG), are recorded by microphones typically placed at one of the common heart auscultation sites. These sites include the aortic, pulmonic, tricuspid, and mitral areas on the chest. The PCG recordings are essentially comprised of the fundamental heart sounds, S1 and S2, commonly referred to the "lub" and "dub" sounds, respectively. In addition to these normal heart sounds, relatively weak S3 and S4 heart sounds in individuals with risks of heart failure, and other abnormal sounds such as opening snap, ejection sound, murmurs, and mid-systolic clicks, may also be present. The application of digital signal processing and machine learning techniques to these PCG signals can overcome the limitations of manual auscultation for effective clinical diagnosis using heart sounds. However, automated classification of heart sounds is not trivial as PCG can be obscured by background noise, breathing sounds, intestinal sounds, and sensor motion against the body. Continuous monitoring of heart sounds using novel wearable medical device sensors with sophisticated algorithms may emerge for screening or diagnosing abnormal heart conditions/defects, which would allow for early and appropriate medical intervention.

Automated classification of heart sound pathologies has been evolving over the last decade using various features extractions involving signal amplitudes, frequencies, wavelets, time-frequency spectral measures, and statistical methods in conjunction with segmentation and classifier methods. However, mass screening for structural heart disease employing a continuous wearable sensor device capable of measuring plurality of physiological signals including ECG, PPG, and accelerometer that allows accurate heart sound segmentation and classification into normal versus abnormal classes at hospital or in-home environment remains a challenge.

Auditory filter models are designed to imitate the way human ear filters sound using an array of independent bandpass filters that recognize and discriminate sound signals effectively at low frequencies more closely than high frequencies. This ability to discern changes more closely at low frequencies is a useful feature for PCG analysis since the spectral power of most heart sounds primarily occur and overlap at low frequencies, particularly under 200 Hz. While auditory filter models are successfully applied in speech analysis, they are relatively unexplored in heart sound classification. Previous studies involving auditory filter model for PCG analysis include noise detection and assessment of the patent ductus arteriosis.

Therefore, there is a strong need for a solution that overcomes the aforementioned issues. The present invention addresses such a need.

SUMMARY

A method of screening of structural heart disease using a wearable sensor device measuring one or more leads of electrocardiogram, phonocardiogram, and accelerometer signals at chest skin surface is disclosed. The method includes measuring electrocardiogram, phonocardiogram, and accelerometer signals on a patient's skin surface; dividing the measured signals into one or more sequences based on a measure of body acceleration; screening decisions on one or more sequences of electrocardiogram and phonocardiogram derived features; determining sequences of aggregate screening decisions; and combining individual decisions to screen for structural heart disease.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present application.

FIG. 2 illustrates a flow chart for screening structural heart disease.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques to those skilled in the art may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with or in combination with other embodiments whether or not explicitly described.

Figure 1:
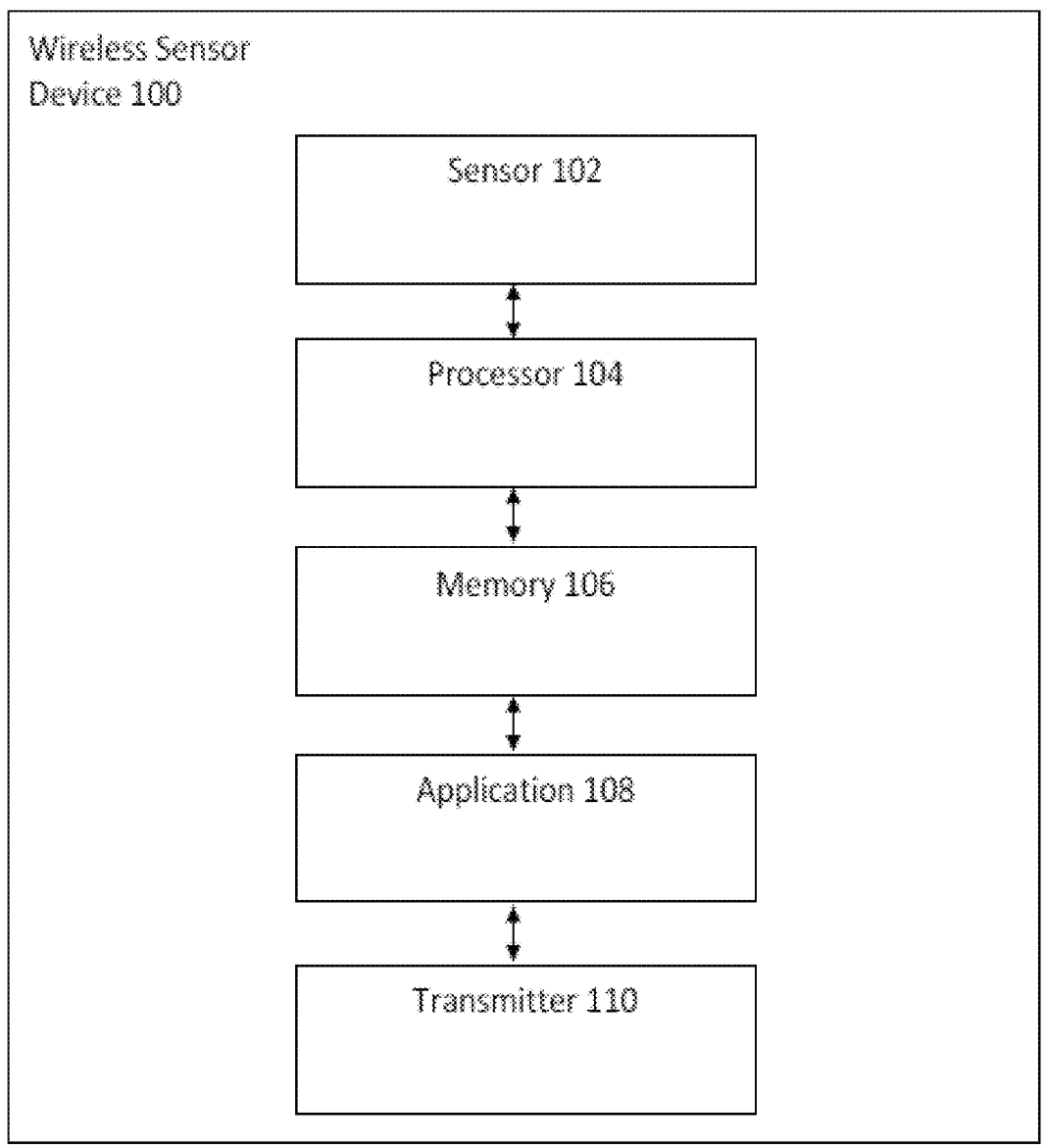
FIG. 1 illustrates a wireless wearable sensor device for health monitoring in accordance with an embodiment.

FIG. 1 illustrates a wireless wearable sensor device 100 for measuring an electrocardiogram (ECG), phonocardiogram (PCG), and accelerometer (ACC) signals on a patient's skin surface, e.g., on the patient's chest. The wireless wearable sensor device 100 or wearable device includes a sensor(s) 102, a processor 104 coupled to the sensor(s) 102, a memory 106 coupled to the processor 104, a wireless wearable sensor device application 108 coupled to the memory 106, and a transmitter 110 coupled to the wireless wearable sensor device application 108.

The wireless wearable sensor device 100 is attached to a user to measure an ECG, PCG, and ACC signals on a patient's skin surface, e.g., on the patient's chest. The sensor(s) 102 includes, but is not limited to, a single-lead or multi-lead ECG, uni-axial or multi-axial accelerometer, and PCG sensors. The sensor(s) 102 obtains an ECG, PCG, and ACC signals on a patient's skin surface which is transmitted to the memory 106 and in turn to the wireless wearable sensor device application 108 via the processor 104. The memory 106 may be a flash memory. The processor 104 executes the wireless wearable sensor device application 108 to process and obtain information regarding the user's health. The information may be sent to the transmitter 110 and transmitted to another user or device for further processing, analysis, and storage. That is, the transmitter 110 may transmit the various ECG, PCG, and ACC data to a remote device/server (e.g. smartphone, cloud-based server) for processing, analysis, and storage. The transmitter 110 may be a Bluetooth Low Energy (BLE) transceiver. Alternatively, the wireless wearable sensor device 100 may process and analyze the temperature data locally via the wireless wearable sensor device application 108 stored in memory 106 and implemented by the processor 104.

The processor 104 is any of a microprocessor and a reusable electronic module. One of ordinary skill in the art readily recognizes that a variety of devices can be utilized for the sensor(s) 102, the processor 104, the memory 106, the wireless wearable sensor device application 108, and the transmitter 110 and that would be within the spirit and scope of the present application.

The wireless wearable sensor device 100 may be an ultra-low cost and fully disposable battery-operated adhesive biometric patch biosensor with integrated sensors and a Bluetooth Low Energy (BLE) transceiver that is attached to the user's skin and used in conjunction with the electronic module to detect, record, and analyze a plurality of ECG, PCG, and ACC signals. The wireless wearable sensor device 100 continuously gathers ECG, PCG, and ACC signals from the patch wearer. The wireless wearable sensor device 100 may then encrypt and transmit the encrypted data via bi-directional communication to a Hub Relay, which in turn transfers the data to a Secure Server where it is stored for viewing, downloading, and analysis. With this information, the healthcare provider can observe improvement or degradation of patient's structural heart disease and intervene if necessary. To improve delivery of biosensor events, events—including live events—are saved to flash memory on the wireless wearable sensor device 100 to avoid data loss. By storing data locally, the wireless wearable sensor device 100 does not need to maintain a constant Bluetooth connection. No data is lost when the wearer is out of Bluetooth range for example and reconnection occurs automatically when the wireless wearable sensor device 100 is within range of the Hub Relay. When the wireless wearable sensor device 100 has a connection to the relay, the wireless wearable sensor device 100 transmits data at regular intervals, and receives confirmation from the relay of successful transmission. The wireless wearable sensor device 100 may include onboard flash memory that stores firmware, configuration files, and sensor data. The healthcare provider can configure how the sensor collects data. Individual data streams (such as ECG, PCG, and ACC signals) may be enabled or disabled, depending on how the biosensor will be used.

The ECG, PCG, and ACC signals are then processed, filtered, modeled, and analyzed using either integrated processors and algorithms of the wearable device 100 (e.g. the reusable electronic module or system-on-chip board) or an external processing device (e.g. smartphone device, cloud-based server network).

Additionally, one of ordinary skill in the art readily recognizes that a variety of wireless wearable sensor devices can be utilized including but not limited to wearable devices, that would be within the spirit and scope of the present application.

The solutions further described herein pertain to the application of auditory filter models for accurate classification of heart sound signals segmented using ECG derived fiducial features and probabilistic sequencing of physiological events using plurality of signals.

FIG. 2 illustrates a flow chart 200 for an example implementation of operations taken for screening structural heart disease, in accordance with the example embodiments described herein. The example embodiments may include methods, programs (e.g., computer-executable instructions and components), systems, apparatuses, and/or devices.

By this example, a wearable sensor measures an electrocardiogram (ECG), phonocardiogram (PCG), and accelerometer (ACC) signals on a patient's skin surface, e.g., on the patient's chest at 210. In accordance with at least one example embodiment, a signal may be divided into one or more sequences based on a measure of body acceleration derived from the accelerometer data at 220. A screening algorithm may be applied individually, i.e. screening decisions, on each sequence of ECG and PCG signal at 230 to determine structural heart disease. The screening outputs of individual sequences are aggregated, i.e. determine sequence of aggregate screening decisions at 240. The final screening decision may be determined from the individual decisions by combining individual decisions to screen for structural heart disease at 250.

Figure 3:
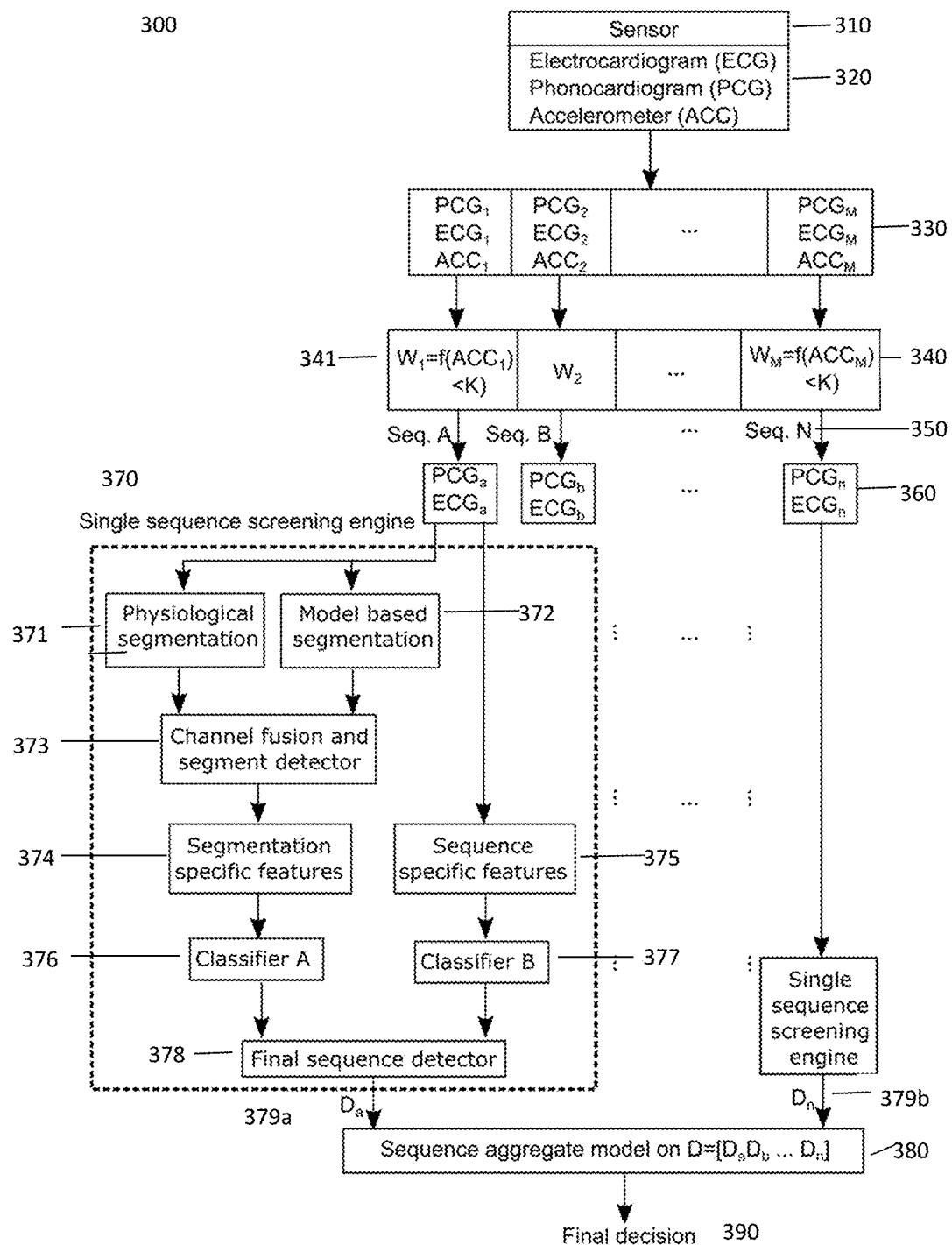
FIG. 3 illustrates a block diagram for an implementation of operations taken for screening structural heart disease.

More details of the above system and method for screening structural heart disease are illustrated in flowchart 300 in FIG. 3. The sensor system 310 includes a single-lead or multi-lead ECG, uni-axial or multi-axial accelerometer, and PCG sensors 320. The form factor of wearable sensor devices include example embodiments such as adhesive patch sensors, chest-bands, or one or more electronic modules adhered to a patient's body. The signals may be filtered to remove noise and aligned in time taking into account any propagation delay. Then the time aligned ECG, PCG, and accelerometer signals 330 are divided into windows $W_i$ 340 of arbitrary durations to obtain $x_i(t)$, $y_i(t)$, and $z_i(t)$ respectively where i is the window number, and $1 \leq i \leq M$. In each window $W_i$, a measure of body acceleration may be computed as function of $z_i(t)$ and compared to threshold K, such that $W_i = (f(z_i(t)) < K)$ 341, where $W_i \in (0,1)$. If $W_i = 1$, then that window containing $x_i(t)$ and $y_i(t)$ is used for further analysis; otherwise that window may be invalidated or discarded from the analysis. The function $f(z_i(t))$ may simply be a linear combination of Riemann sum of filtered $z_i(t)$, or it may be learned from data to differentiate intensity of body acceleration. In this way, N sequences 350 may be selected from M windows of $x_i(t)$, $y_i(t)$, and $z_i(t)$ based on the accelerometer data. The sequences may be denoted by $S_j$, and include $x_j(t)$ and $y_j(t)$ where j is the sequence number, $1 \leq j \leq N$, and $N \leq M$. Each sequence $S_j$ 360 is then fed individually into a sequence screening engine to detect structural heart abnormality in that sequence.

The sequence screening engine 370 relies on two categories of features, including segmentation specific features 374 and sequence specific features 375 to screen $S_j$. Segmentation specific features may be derived after segmenting the heart sounds into the constituent heart phases such as S1, systole, S2, and diastole for each heartbeat contained in $y_j(t)$. Single channels of segmentation such as physiological segmentation 371 and model based segmentation 372 are employed independently to determine the constituent heart stages. Then the weighted sum of single channel detections may be used to obtain the final position of the segments. The sequence specific features are derived directly from $y_j(t)$ without any segmentation.

Figure 4A:
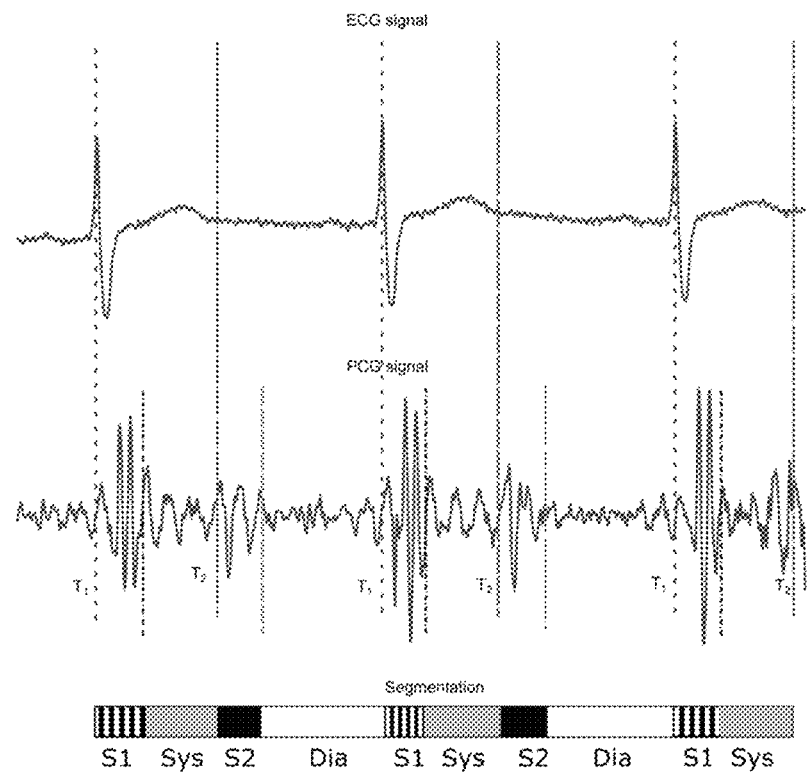
FIG. 4a illustrates an exemplary process of physiological segmentation.

FIG. 4a illustrates physiological segmentation 371 which includes determining the fiducial points in $x_j(t)$ such as peak of R wave, and end of T wave for each heartbeat. Then the time duration between peak of R wave ($T_1$) and end of T wave ($T_2$) of a beat from $x_j(t)$ is used to determine the locations of S1 and systole (Sys) in $y_j(t)$ as illustrated in FIG. 4a. Likewise, the time duration between end of T wave of a beat and peak of R wave of next beat from $x_j(t)$ is used to determine the locations of S2 and diastole (Dia) in $y_j(t)$. The boundary between S1 and systole, and S2 and diastole may be learned from the training set.

Figure 4B:
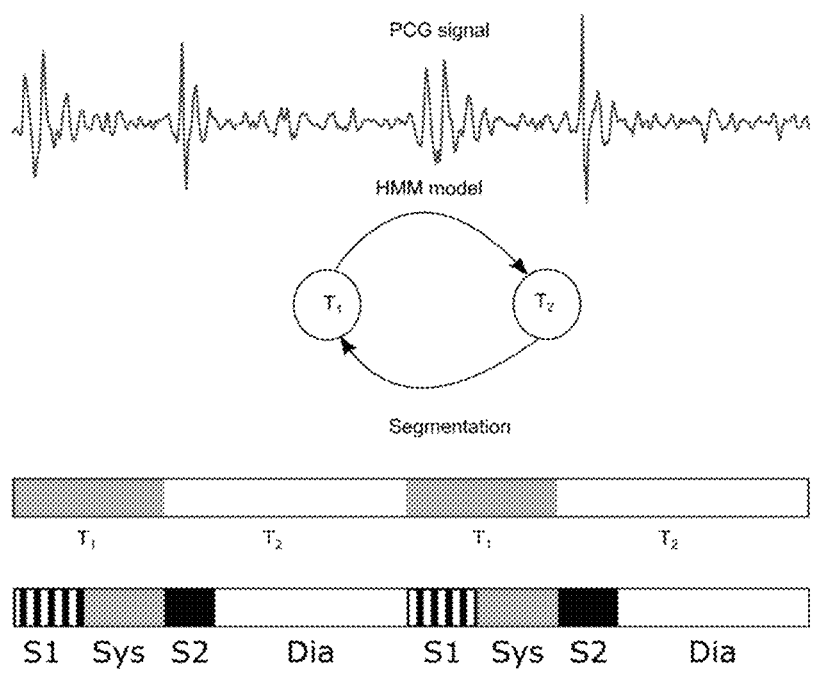
FIG. 4b illustrates an exemplary process of model based segmentation.

Model based segmentation 372 includes determining the fiducial points in $y_j(t)$ using Hidden Markov based model (HMM). As an example, PCG signals $y_j(t)$ may be filtered using a $2^{nd}$ order Butterworth bandpass filter between 25 and 400 Hz, and resampled uniformly at $F_s = 1000$ Hz. An illustration of this process for determining $T_1$ and $T_2$ is shown in FIG. 4b. The expected duration of $T_1$ and $T_2$ is modeled using a probabilistic distribution, and the model may be trained to derive the emission probabilities of the HMM. Specifically, the true states $Q = \{q_1, q_2, \ldots, q_t\}$ are unknown, but the observed sequence O is known. Thus, the model finds the state sequence that is most likely to produce the observed state:

$$Q^* = \arg \max_Q P(Q|O,\lambda)$$

where $Q^*$ is the state sequence that is most likely to produce O, the observed state sequence, and $\lambda$ denotes the model parameters such as the HMM's transition matrix, and the aforementioned duration distribution. $T_1$ and $T_2$ are divided into S1 and systole, and S2 and diastole respectively, where the boundaries are learned from the training set. Further, segmentation can also include a subset of these heart phases.

The weighted sum of single channel detections (physiological and model based segmentation) may be compared to a threshold to obtain determine the final position of the segments, i.e. channel fusion and segment detector of 373.

Features may be extracted based on the output of segmentation as well as directly from $y_j(n)$. The following is an example of extracting Segmentation specific features 374 and sequence specific features 375 based on auditory frequency cepstral coefficients (AFCC).

First, the PCG signal, $y(n)$, may be divided into i frames, of duration, d, with some overlap, assuming the audio frequencies are relatively stationary in these time frames. Secondly, the power spectrum in each frame, $P_i(k)$, may be calculated by applying a Hanning window $w(n)$ of length N to reduce the spectral leakage as given below that estimates the amount of energy at different frequencies within the signal, similar to the functioning of the cochlea:

$$P_i(k) = \frac{1}{N} \left| \sum_{n=0}^{N-1} x_i(n) w(n) e^{-i2\pi n \frac{k}{N}} \right|^2$$

where $w(n) = 0.5 - 0.5\cos\left(\frac{2\pi n}{N-1}\right)$ and $k \in [0, N-1]$.

Thirdly, an M-channel auditory filterbank $h(m, k)$ may be applied to the power spectral estimates, where $m \in [1, M]$ and M is the total number of filters. The auditory filterbank may belong to the rounded exponential family, the gammatone family, including gammachirp and all-pole variants, and the filter cascades, both all-pole and pole-zero variants, as well as their non-linear extensions. Taking the logarithm of the calculated sum of the energy within each filter of auditory filterbank further distinguishes closely spaced frequencies effectively similar to the human cochlea auditory system perceiving sounds.

$$g_{i,m} = \log\left(\sum_{k=0}^{N-1} h(m, k) P_i(k)\right)$$

Finally, discrete cosine transform may be applied to decorrelate the logarithm of the filterbank energies, and obtain the coefficients $c_{i,j}$ corresponding to the $j^{th}$ AFCC for the $i^{th}$ frame.

$$c_{i,j} = \sum_{m=1}^{M} g_{i,m} \cos\left(\frac{\pi j(2m-1)}{2M}\right)$$

In the case of segmentation specific features 374, the feature vector may be calculated by applying statistical measures such as mean, standard deviation, or higher order moments on each coefficient across the frames of each of the phases of the heart cycle, as determined by the weighted sum of single channel segmentations. The total number of features computed with segmentation is equal to $n_c*n_p*n_s$ where $n_c$ is the number of extracted coefficients, $n_p$ is the number of phases of the segmented heart cycle, and $n_s$ is the number of statistical measures used. On the other hand, the sequence specific feature 375 vector without segmentation may be calculated by applying statistical measures on each coefficient across all frames and the total number of features is equal to $n_c*n_s$.

Classification may be performed for the segmentation specific features and sequence specific features independently using Classifier A 376 and Classifier B 377. The classifier may belong to machine learning algorithms such as logistic regression, support vector machines, artificial neural networks, gradient boosting, etc. As an example, weighted SVM classifier with a radial basis function (RBF) kernel, $e^{(-\gamma|x_i-x_j|^2)}$ can be used as classifier. The hyperparameters of this classifier include the misclassification penalty, C and the kernel coefficient for the radial basis function kernel, y which are optimized as described in the subsequent section.

The weighted SVM addresses the unequal proportion of normal and abnormal heart sound recordings in clinical situations with the cost function for a set of weights, w defined as:

$$L(w) = \frac{\|w\|^2}{2} + C^+\left(\sum_{i: y_i=+1}^{N} \xi_i\right) + C^-\left(\sum_{i: y_i=+1}^{N} \xi_i\right)$$

where $C^+$ and $C^-$ are the regularization or penalty term for the normal and abnormal heart sound classes respectively. The weighted classes $C^j$ are obtained by $$C^j = C*\left(\frac{n}{kn_j}\right),$$

where n is the total number of heart sound observations, k is the number of classes, and $n_j$ is the number of observations in class j. The hyperparameters for feature extraction and classifier such as M, subset of the coefficients $c_{i,j}$, C and γ are optimized by maximizing the average of sensitivity (the probability of correctly identifying an abnormal case), and specificity (the probability of correctly identifying a normal case). While it is common in speech signal processing to use more than 20 channels and the first 10 coefficients of the auditory filterbank, there is no substantial improvement in the classification performance beyond 10 channels during optimization. Hence, M and subset of $c_{i,j}$ may be optimized on a 2-d grid of 10 channels×10 coefficients independently for different combinations of statistical measures. The classifier hyperparameters are optimized initially using a coarse grid search and then fine-tuned on $C \in [2^0, 2^4]$ and $\gamma \in [2^{-4}, 2^0]$. The output of the classifiers A and B are combined at 378, i.e. final sequence detector, based on a linear or non-linear rule to determine the decision $D_j$ 379. Thus, sequence screening engine takes $S_j$ as inputs to determine the screening results $D_j$.

Figure 5:
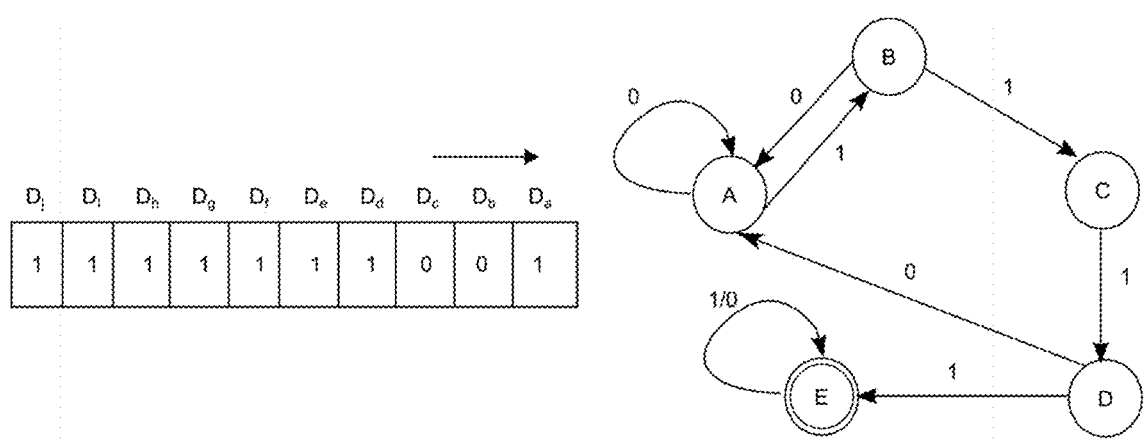
FIG. 5 illustrates sequence aggregation from sequence screening engines and finite state machine.

The screening outputs $D_j$ 379a and 379b may be aggregated into a vector $D=[D_a D_b \ldots D_n]$ and fed into the sequence aggregate model at 380 to determine the final decision. The screening outputs $D_j$ 379a and 379b may be binary (1, 0), categorical, numerical (0, 1, 2, 3, 4, . . . ). The sequence aggregate model may be a weighted combination of voting schemes, recurrent neural networks, and finite state machines to recognize a sequence. FIG. 5 shows an example embodiment of sequence aggregation and state machine to identify four consecutive positive sequences, that is, an example of sequence aggregation from sequence screening engines and finite state machine to identify the final screening sequence 1111. The symbol $D_a$ is fed initially to state A; then, based on the next symbol $D_b$ it transitions to the next state (in this case state A), and so forth, until it reaches the final state E which indicates presence of structural heart disease. The voting schemes such as be majority voting, and threshold crossing, recurrent neural networks and its variants such as long short term memory, gated recurrent units, and bidirectional networks are within the scope of the invention. Thus the final screening decision 390 may be obtained to screen for structural heart disease.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Furthermore, the present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and even apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Figure 6:
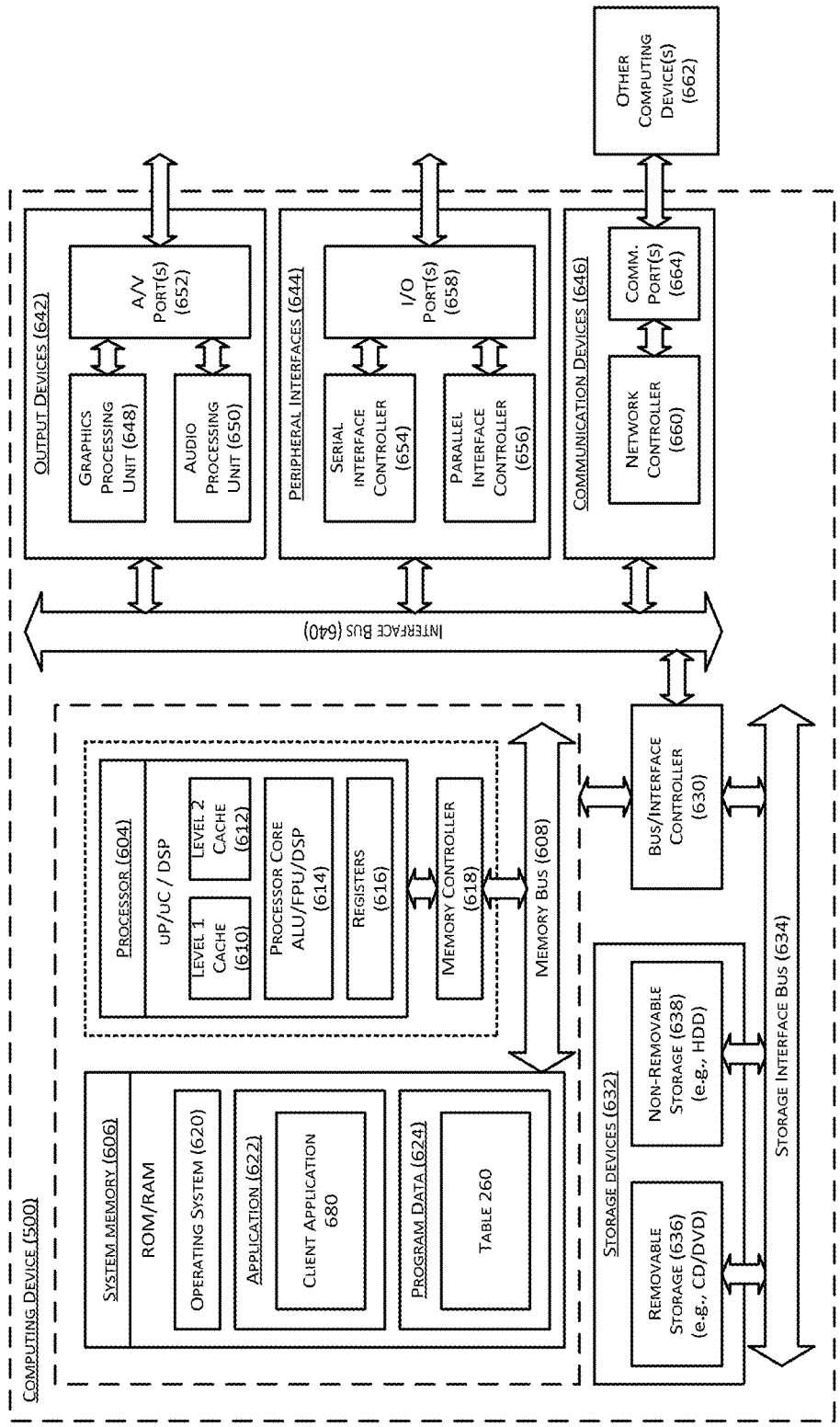
FIG. 6 illustrates a block diagram of a computing device.

FIG. 6 shows sample computing device 600 in which various embodiments of the wearable sensor in a ubiquitous computing environment may be implemented. More particularly, FIG. 6 shows an illustrative computing embodiment, in which any of the operations, processes, etc. described herein may be implemented as computer-readable instructions stored on a computer-readable medium. The computer-readable instructions may, for example, be executed by a processor of a mobile unit, a network element, and/or any other computing device.

In a very basic configuration 602, computing device 600 typically includes one or more processors 604 and a system memory 606. A memory bus 608 may be used for communicating between processor 604 and system memory 606.

Depending on the desired configuration, processor 604 may be of any type including but not limited to a microprocessor (μP), a microcontroller (μC), a digital signal processor (DSP), or any combination thereof. Processor 604 may include one more levels of caching, such as level one cache 610 and level two cache 612, processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624.

Application 622 may include Client Application 680 that is arranged to perform the functions as described herein including those described previously with respect to FIGS. 1-5. Program data 624 may include Table 650, which may alternatively be referred to as "figure table 650" or "distribution table 650," which may be useful for measuring ECG, PCG, and ACC signals on a patient's skin surface as described herein.

Computing device 600 may have additional features or functionality, and additional interfaces to facilitate communications between basic configuration 602 and any required devices and interfaces. For example, bus/interface controller 630 may be used to facilitate communications between basic configuration 602 and one or more data storage devices 632 via storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636, and non-removable storage devices 638 are examples of computer storage media. Computer storage media may include, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include interface bus 640 for facilitating communication from various interface devices, e.g., output devices 642, peripheral interfaces 644, and communication devices 646, to basic configuration 602 via bus/interface controller 630. Example output devices 642 may include graphics processing unit 648 and audio processing unit 650, which may be configured to communicate to various external devices such as a display or speakers via one or more A/V ports 652. Example peripheral interfaces 644 may include serial interface controller 654 or parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 458. An example communication device 646 may include network controller 660, which may be arranged to facilitate communications with one or more other computing devices 662 over a network communication link via one or more communication ports 664.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 400 may also be implemented as a personal computer including both laptop computer and non-laptop computer configurations.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein may be implemented, e.g., hardware, software, and/or firmware, and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes for determining patient body temperature via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Lastly, with respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims, e.g., bodies of the appended claims, are generally intended as "open" terms, e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an," e.g., "a" and/or "an" should be interpreted to mean "at least one" or "one or more;" the same holds true for the use of definite articles used to introduce claim recitations. In addition, even if a specific number of an introduced claim recitation is explicitly recited, those skilled in the art will recognize that such recitation should be interpreted to mean at least the recited number, e.g., the bare recitation of "two recitations," without other modifiers, means at least two recitations, or two or more recitations. Furthermore, in those instances where a convention analogous to "at least one of A, B, and C, etc." is used, in general such a construction is intended in the sense one having skill in the art would understand the convention, e.g., "a system having at least one of A, B, and C" would include but not be limited to systems that have A alone, B alone, C alone, A and B together, A and C together, B and C together, and/or A, B, and C together, etc. In those instances where a convention analogous to "at least one of A, B, or C, etc." is used, in general such a construction is intended in the sense one having skill in the art would understand the convention, e.g., "a system having at least one of A, B, or C" would include but not be limited to systems that have A alone, B alone, C alone, A and B together, A and C together, B and C together, and/or A, B, and C together, etc. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method of screening of structural heart disease using a wearable sensor device measuring one or more leads of electrocardiogram, phonocardiogram, and accelerometer signals at chest skin surface, the method comprising:
measuring, by at least one sensor, electrocardiogram (ECG), phonocardiogram (PCG), and accelerometer (ACC) signals on a patient's skin surface and sending the ECG, PCG, and ACC signals to a processor;
executing, by the processor, an application stored in a memory to:
filter the ECG, PCG, and ACC signals to remove noise;
align the filtered ECG, PCG, and ACC signals in time, taking into account any propagation delay;
divide the measured signals into one or more sequences based on a measure of body acceleration,
wherein the dividing the measured signals into one or more sequences based on a measure of body acceleration includes the time aligned ECG, PCG, and ACC signals are divided into respective windows of arbitrary durations to obtain the one or more sequences;
screen decisions on the one or more sequences of the ECG and PCG derived features;
determine sequences of aggregate screening decisions; and
combine the aggregate screening decisions to screen for structural heart disease and output an indication of a presence of the screened structural heart disease to a display.

2. The method of claim 1, wherein the measure of body acceleration is derived from the accelerometer signals.

3. The method of claim 1, wherein the screening decisions includes applying a screening algorithm on the one or more sequences of the electrocardiogram and phonocardiogram derived features.

4. The method of claim 1, wherein the screening decisions on one or more sequences of electrocardiogram and phonocardiogram derived features includes feeding each sequence individually into a sequence screening engine, wherein the sequence screening engine relies on two categories of features, including criteria for sequencing data.

5. The method of claim 4, wherein the criteria for sequencing data segmentation specific features are derived after segmenting the PCG signals into constituent heart phases including S1, systole, S2, and diastole for each heartbeat.

6. The method of claim 4, wherein the screening decisions on one or more sequences of electrocardiogram and phonocardiogram derived features further includes employing independently single channels of segmentation including physiological segmentation and model based segmentation to determine constituent heart stages.

7. The method of claim 6, wherein a weighted sum of single channel are used to obtain a final position of the segmentation.

8. The method of claim 1, further comprising directly deriving sequence specific features from the second sequence without any segmentation.

9. The method of claim 1, wherein the combining individual decisions to screen for the structural heart disease includes aggregating the screening and fed into a sequence aggregate model to determine a final decision for the structural heart disease.

10. A method of screening of structural heart disease using a wearable sensor device measuring one or more leads of electrocardiogram, phonocardiogram, and accelerometer signals at chest skin surface, the method comprising:
measuring, by at least one sensor, electrocardiogram (ECG), phonocardiogram (PCG), and accelerometer (ACC) signals on a patient's skin surface and sending the ECG, PCG, and ACC signals to a processor;
executing, by the processor, an application stored in a memory to:
divide the measured signals into one or more sequences based on a measure of body acceleration;
screen decisions on the one or more sequences of the ECG and PCG derived features;
determine sequences of aggregate screening decisions;
combine the aggregate screening decisions to screen for structural heart disease; and
output an indication of a presence of the screened structural heart disease to a display;
wherein the screening decisions on one or more sequences of electrocardiogram and phonocardiogram derived features includes feeding each sequence individually into a sequence screening engine, wherein the sequence screening engine relies on two categories of features, including segmentation specific features and sequence specific features to screen the sequence;
wherein the screening decisions on one or more sequences of electrocardiogram and phonocardiogram derived features further includes employing independently single channels of segmentation including physiological segmentation and model based segmentation to determine constituent heart stages; and
wherein the physiological segmentation includes:
determining fiducial points in a first sequence including a peak of an R wave, and an end of a T wave for each heartbeat;
determining locations of S1 and systole (Sys) in a second sequence by using a time duration between peak of R wave ($T_1$) and end of T wave ($T_2$) of a beat from the first sequence;
determining locations of S2 and diastole (Dia) in the second sequence by using a the time duration between an end of T wave of a beat and peak of R wave of a next beat from the first sequence; and
learning the boundary between the S1 and systole, and the S2 and diastole from a training set.

11. The method of claim 6, wherein the model based segmentation includes:
determining fiducial points in the second sequence using Hidden Markov based model (HMM); and
dividing $T_1$ and $T_2$ into heart phases of S1 and systole, and S2 and diastole, respectively; and
learning boundaries from a training set.

12. The method of claim 11, wherein the model based segmentation further includes a subset of the heart phases.

13. A method of screening of structural heart disease using a wearable sensor device measuring one or more leads of electrocardiogram, phonocardiogram, and accelerometer signals at chest skin surface, the method comprising:
measuring, by at least one sensor, electrocardiogram (ECG), phonocardiogram (PCG), and accelerometer (ACC) signals on a patient's skin surface and sending the ECG, PCG, and ACC signals to a processor;

executing, by the processor, an application stored in a memory to:

divide the measured signals into one or more sequences based on a measure of body acceleration;

screen decisions on the one or more sequences of the ECG and PCG derived features;

determine sequences of aggregate screening decisions;

combine the aggregate screening decisions to screen for structural heart disease; and output an indication of a presence of the screened structural heart disease to a display;

wherein the screening decisions on one or more sequences of electrocardiogram and phonocardiogram derived features includes feeding each sequence individually into a sequence screening engine, wherein the sequence screening engine relies on two categories of features, including segmentation specific features and sequence specific features to screen the sequence;

wherein the screening decisions on one or more sequences of electrocardiogram and phonocardiogram derived features further includes employing independently single channels of segmentation including physiological segmentation and model based segmentation to determine constituent heart stages; and wherein a weighted sum of single channel detections of the physiological and model based segmentation is compared to a threshold to determine a final position of the segments.

14. The method of claim 13, wherein features are extracted based on at least one of the output of segmentation or from the second sequence.

15. The method of claim 14, wherein classification is performed for the segmentation specific features and sequence specific features independently using Classifier A and Classifier B, respectively, wherein the Classifier A and the Classifier B includes machine learning algorithms including at least one of: logistic regression, support vector machines, artificial neural networks, or gradient boosting.

16. The method of claim 15, wherein the output of the classifiers A and B are combined at a final sequence detector, based on a linear or non-linear rule to determine a decision $D_j$.

* * * * *